US011312878B2

(12) United States Patent
Son et al.

(10) Patent No.: US 11,312,878 B2
(45) Date of Patent: Apr. 26, 2022

(54) AQUEOUS COMPOSITION FOR PREPARING HARD CAPSULE, PREPARATION METHOD THEREFOR, HARD CAPSULE, AND METHOD FOR RECYCLING HARD CAPSULE SCRAPS

(71) Applicant: SAMSUNG FINE CHEMICALS CO., LTD., Ulsan (KR)

(72) Inventors: Jin Ryul Son, Incheon (KR); Sang Youb Lee, Incheon (KR); Jyung Hee Jeon, Incheon (KR); Sung Hwan Bang, Incheon (KR); Ju Hee Shin, Incheon (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 740 days.

(21) Appl. No.: 14/415,006

(22) PCT Filed: Jul. 4, 2013

(86) PCT No.: PCT/KR2013/005927
§ 371 (c)(1),
(2) Date: Jan. 15, 2015

(87) PCT Pub. No.: WO2014/017756
PCT Pub. Date: Jan. 30, 2014

(65) Prior Publication Data
US 2015/0197655 A1 Jul. 16, 2015

(30) Foreign Application Priority Data

Jul. 23, 2012 (KR) .................. 10-2012-0080258
Nov. 20, 2012 (KR) .................. 10-2012-0131947

(51) Int. Cl.
| | |
|---|---|
| *C09D 101/28* | (2006.01) |
| *A61K 9/48* | (2006.01) |
| *C08J 11/08* | (2006.01) |
| *C09D 105/00* | (2006.01) |
| *C09D 105/06* | (2006.01) |

(52) U.S. Cl.
CPC ........ *C09D 101/284* (2013.01); *A61K 9/4816* (2013.01); *A61K 9/4866* (2013.01); *C08J 11/08* (2013.01); *C09D 101/28* (2013.01); *C09D 105/00* (2013.01); *C09D 105/06* (2013.01); *C08J 2301/26* (2013.01); *Y02W 30/62* (2015.05)

(58) Field of Classification Search
CPC ...... A61K 9/48; A61K 9/4816; A61K 9/4866; B29C 39/10; C09D 101/284; C09D 101/28; C09D 105/00; C09D 105/06; C08J 11/08; C08J 2301/26; Y02W 30/62
USPC .......................................... 427/394
See application file for complete search history.

(56) References Cited

U.S. PATENT DOCUMENTS

| | | | |
|---|---|---|---|
| 3,493,407 | A | 2/1970 | Greminger et al. |
| 4,402,692 | A | 9/1983 | Takagishi |
| 4,917,885 | A | 4/1990 | Chiba et al. |
| 6,410,050 | B1 | 6/2002 | Yang |
| 6,413,463 | B1 | 7/2002 | Yamamoto et al. |
| 6,649,180 | B1 | 11/2003 | Matsuura et al. |
| 2001/0036472 | A1* | 11/2001 | Wong .................. A61K 9/0004 424/456 |
| 2004/0022845 | A1 | 2/2004 | Zhang |
| 2005/0112189 | A1* | 5/2005 | Motoune et al. ........ A61K 9/48 424/451 |
| 2007/0254024 | A1* | 11/2007 | Cade .................... A61K 9/4816 424/451 |
| 2010/0212261 | A1 | 8/2010 | Boldis et al. |

FOREIGN PATENT DOCUMENTS

| | | |
|---|---|---|
| CN | 1326733 A | 12/2001 |
| CN | 1745745 A | 3/2006 |
| CN | 101167705 A | 4/2008 |
| EP | 1029539 | 8/2000 |
| EP | 1849461 A1 | 10/2007 |
| EP | 2476439 | 7/2012 |
| EP | 2476439 A1 | 7/2012 |
| JP | 03009755 A | 1/1991 |
| JP | 2000136126 A | 5/2000 |
| JP | 2001245609 A | 9/2001 |
| JP | 2005187412 | 7/2005 |
| JP | 2005187412 A | 7/2005 |
| JP | 2010202550 A | 9/2010 |
| KR | 1020000057602 | 9/2000 |
| KR | 1020010033693 | 4/2001 |
| KR | 1020060103566 | 10/2006 |
| KR | 1020090057470 A | 6/2009 |
| MX | 2009004434 A | 4/2009 |
| WO | 2006082842 A1 | 8/2006 |
| WO | 2007003113 A1 | 1/2007 |
| WO | 2011030952 | 3/2011 |
| WO | 2011155686 | 12/2011 |
| WO | 2014088177 A1 | 6/2014 |
| WO | 2000010538 A | 3/2020 |

OTHER PUBLICATIONS

Chinese Office Action for Chinese Application No. 201380039127.8 dated Oct. 20, 2016, citing the above reference(s).
International Search Report for International Application No. PCT/KR2013/005927 dated Sep. 30, 2013.
(Continued)

*Primary Examiner* — Ling Siu Choi
*Assistant Examiner* — Ronald Grinsted
(74) *Attorney, Agent, or Firm* — Cantor Colburn LLP

(57) ABSTRACT

Disclosed are an aqueous composition for preparing a hard capsule, a preparation method therefor, a hard capsule, and a method for recycling hard capsule scraps. The disclosed aqueous composition for preparing a hard capsule comprises a water-soluble cellulose ether, an alcohol, and water. In addition, the method for recycling hard capsule scraps comprises the step of dissolving hard capsule scraps comprising a water-soluble cellulose ether into a mixture solution comprising water and an alcohol so as to prepare an aqueous composition for preparing a recycled hard capsule.

12 Claims, 1 Drawing Sheet

(56) References Cited

OTHER PUBLICATIONS

Written Opinion for International Application No. PCT/KR2013/005927 dated Sep. 30, 2013.
"Hypromellose" In: "Handbook of pharmaceutical excipients", Fifth edition, Jan. 1, 2006, pp. 346-349, Pharmaceutical Press, London.
Database WPI Week 200866 Thomson Scientific, London, GB; AN 2008-L17215, XP-002754260, 2 Pages, & CN 101 167 705 A (Beijing Long March Tianmin Hi-Tech Co Lt) Apr. 30, 2008.
Extended European Search Report for Application No. 13823894.4-1455 dated Feb. 23, 2016.
Japanese Office Action for Application No. 2015-524168 dated May 11, 2017, citing the above reference(s).
Columbia Office Action for reference file No. 15034483 dated Jun. 29, 2017, citing the above reference(s).
European Office Action for Application No. 13823894.4 dated Jul. 6, 2017 citing the above reference(s).
Taiwanese rejection decision dated Aug. 15, 2017 citing the above reference(s).
Indian Office action for application No. 427/DELNP/2015 dated Nov. 13, 2018, citing the above reference(s).
English Translation of Office Action issued in Argentinian Patent Application No. P 13 01 02603, received Feb. 10, 2021, which corresponds to the above-identified application.
Office Action issued in Argentinian Patent Application No. P 13 01 02603, received Feb. 10, 2021, which corresponds to the above-identified application.

* cited by examiner

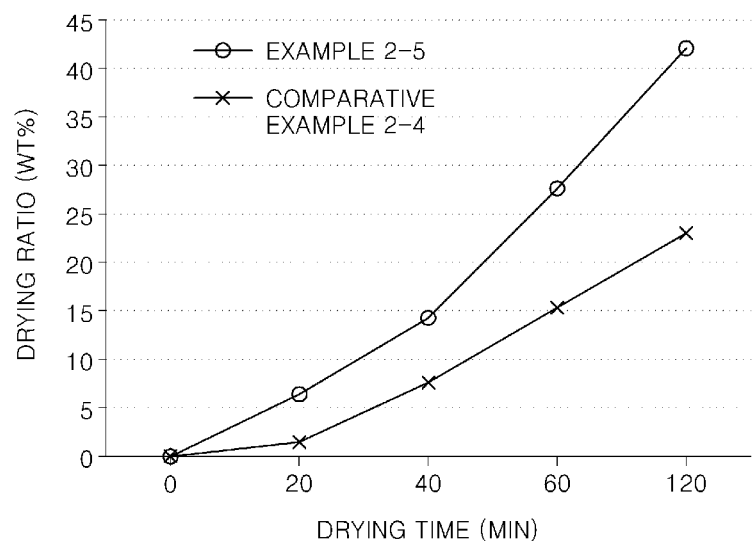

AQUEOUS COMPOSITION FOR PREPARING HARD CAPSULE, PREPARATION METHOD THEREFOR, HARD CAPSULE, AND METHOD FOR RECYCLING HARD CAPSULE SCRAPS

TECHNICAL FIELD

One or more embodiments of the present invention relate to an aqueous composition for preparing a hard capsule, a method of preparing the same, a hard capsule prepared by using the aqueous composition, and a method of recycling a hard capsule scrap. In particular, one or more embodiments of the present invention relate to an aqueous composition for preparing a hard capsule, including a water-soluble cellulose ether and an alcohol, a method of preparing the same, a hard capsule prepared by using the aqueous composition, and a method of cycling a hard capsule scrap which is produced when a hard capsule is prepared.

BACKGROUND ART

In general, hard capsules have been prepared by using gelatin derived from bovines or swine. A Scrap, which is produced in the manufacturing procedure of a gelain hard capsule, has the same gel characteristics as gelatin, when the scrap is dissolved in high-temperature water and then cooled to room temperature. Accordingly, the scrap can be recycled as a hard capsule. Thus, when a hard capsule is prepared by using gelatin, capsule production costs may reduce, which is why most capsule manufacturers prefer to the production of a gelatin hard capsule.

Gelatin-containing aqueous compositions are prepared for a relatively short time period due to the direct dissolution of gelatin in high-temperature water (for example, 60° C.), and when a mold pin is immersed therein and then taken therefrom to dry the gelatin-containing aqueous compositions coated on the mold pin, the drying time is short and the obtained hard capsule may have excellent elasticity, glossiness, and disintegrability, and the production yield of the hard capsule is very high. However, the recent outbreak of the mad cow diseases reduces use of gelatin, and accordingly, capsules prepared by using cellulose ether that is a vegetable material, instead of the gelatin, are getting much attention.

However, although cellulose ether is dissolved in room temperature (25° C.) water, immediately when added into water, most of the cellulose ether aggregates to form an aggregate, requiring a long time for complete dissolution. To prevent this problem, when an aqueous composition for preparing a hard capsule is prepared, cellulose ether is added to high temperature (for example, 80° C. or higher) water to prevent the aggregation and then dispersed well to prepare a dispersion, and then the dispersion is naturally cooled down to a first temperature (for example, 40 to 50° C.) to dissolve the dispersed cellulose ether in water. Thereafter, the resultant is heated to a second temperature (for example, 55 to 65° C.), and then a gelation agent and optionally a gelation aid are added to the resultant. In this regard, the heating of the resultant to the second temperature is performed to prevent solidification of the gelation agent and gelation aid. However, cellulose ether may not be completely dissolved in water at the second temperature, and thus an aqueous composition and a final hard capsule including cellulose ether may have the following disadvantages:

(1) the aqueous composition may have a varying viscosity according to location and also may undergo a layer-separation during a long-term storage;

(2) a degree of mixing of cellulose ether and a gelation agent (and optionally, a gelation aid) in the aqueous composition may decrease, thereby requiring more of the gelation agent (and optionally, a gelation aid) to be added thereto;

(3) the aqueous composition may have a low filtering efficiency in a subsequent filtering process for removing foreign materials (for example, fiber) therefrom;

(4) even after the filtering, foreign materials may remain in the aqueous composition to deteriorate performance of a capsulation agent and/or a capsulation aid, leading to a decrease in moldability or formability;

(5) when a drying process is performed to evaporate water in the aqueous composition doped on a substrate (for example, mold pin) in a capsule molding process, a drying speed of the aqueous composition is low;

(6) the preparation time and drying time of the aqueous composition are long, and thus, the production yield of a hard capsule is low; and (7) foreign materials remaining in the aqueous composition are included in a hard capsule, which is a final product, and due to the included foreign materials, the quality (elasticity, glossiness, disintegrability, or the like) of the hard capsule decreases, and it is difficult to keep the quality of a hard capsule constant for all production lots.

Also, when a hard capsule is prepared by using cellulose ether, scrap, which is produced in the manufacturing procedure of the hard capsule, forms a high-viscosity solution when dissolved in water. Accordingly, it is difficult for the scrap to be dissolved at high concentration, and also, the high-viscosity solution does not have gel characteristics. Thus, the recycling of the scrap as a hard capsule is difficult.

DETAILED DESCRIPTION OF THE INVENTION

Technical Problem

The present invention provides an aqueous composition for preparing a hard capsule, including a water-soluble cellulose ether and an alcohol.

One or more embodiments of the present invention provide a method of preparing the aqueous composition.

One or more embodiments of the present invention provide a hard capsule prepared by using the aqueous composition.

One or more embodiments of the present invention provide a method of recycling a hard capsule scrap including a water-soluble cellulose ether.

Technical Solution

According to an aspect of the present invention, there is provided a According to an aspect of the present invention, there is provided an aqueous composition for preparing a hard capsule, wherein the aqueous composition includes: a water-soluble cellulose ether; an alcohol; and water.

The aqueous composition may include 10 to 25 wt % of the water-soluble cellulose ether, and 5 to 30 wt % of the alcohol.

The water-soluble cellulose ether may include hydroxypropyl methylcellulose(HPMC), hydroxyethyl methylcellulose(HEMC), methylcellulose(MC), or a mixture of two or more of these.

The alcohol may include ethanol, methanol, isopropanol, butanol, or a mixture of two or more of these.

The aqueous composition may further include 0.05 to 5.0 wt % of a gelation agent selected from Carrageenan, Gellan gum, Xanthan gum, Pectin, and a mixture of two or more of these.

The aqueous composition may further include more than 0 wt % and up to 1.0 wt % of a gelation aid selected from potassium chloride, potassium acetate, calcium chloride, and a mixture of two or more of these.

According to another aspect of the present invention, there is provided a method of preparing an aqueous composition for preparing a hard capsule, wherein the method includes preparing a cellulose ether solution that contains water, an alcohol and a water-soluble cellulose ether, and that is maintained at a first temperature higher than an atmospheric temperature.

The first temperature may be in a range of 40 to 70° C.

The method may further include aging the cellulose ether solution and adding a gelation agent to the cellulose ether solution.

The aging may be performed at a temperature of 40 to 70° C. for 2 to 12 hours.

According to another aspect of the present invention, there is provided a hard capsule prepared by using the aqueous composition.

According to another aspect of the present invention, there is provided a method of recycling a hard capsule scrap, wherein the method includes preparing an aqueous composition for preparing a recycled hard capsule by dissolving the hard capsule scrap including a water-soluble cellulose ether in a mixed solution including water and an alcohol.

The hard capsule scrap may include 90 to 95 parts by weight of the water-soluble cellulose ether, 0.05 to 5.0 parts by weight of a gelation agent, 0 to 1.0 parts by weight of a gelation aid, and 1.0 to 7.0 parts by weight of water.

The step of preparing the aqueous composition for preparing a recycled hard capsule of the method of preparing a hard capsule scrap may be performed by dissolving an additional water-soluble cellulose ether together with the hard capsule scrap in the mixed solution including water and an alcohol.

The method of recycling a hard capsule scrap may further include maintaining the aqueous composition for preparing a recycled hard capsule at a temperature of 40 to 70° C. for 2 to 12 hours.

The method of recycling a hard capsule scrap may further include adding at least one of an additional gelation agent and an additional gelation aid to the aqueous composition for preparing a recycled hard capsule.

The method of recycling a hard capsule scrap may further include coating the aqueous composition for preparing a recycled hard capsule on a substrate and drying the aqueous composition.

The aqueous composition for preparing a recycled hard capsule may include 10 to 25 wt % of the water-soluble cellulose ether and 5 to 30 wt % of the alcohol.

The aqueous composition for preparing a recycled hard capsule may include 0.05 to 5.0 wt % of a gelation agent.

The aqueous composition for preparing a recycled hard capsule may further include more than 0 wt % and up to 1.0 wt % of a gelation aid.

Advantageous Effects

An aqueous composition for preparing a hard capsule according to an embodiment of the present invention includes water-soluble cellulose ether and an alcohol. Due to the inclusion of water-soluble cellulose ether and water, cellulose ether may directly dissolve in water at not only relatively low temperature (for example, 0 to 40□) but also relatively high temperature (for example, 40 to 70□). Accordingly, the preparation time for the aqueous composition may reduce, a drying time for drying the aqueous composition when molding a capsule may reduce, and a production yield of a hard capsule, which is a final product, may increase. Also, a degree of mixing of cellulose ether and a gelation agent (and optionally, a gelation aid) may improve, and thus, even when the gelation agent (and optionally, a gelation aid) is used in small amounts, a high-quality hard capsule may be obtained.

The manufacturing costs for a hard capsule and the disposal costs for a hard capsule scrap may reduce, and the environmental pollution may reduce, and a high-quality hard capsule may be obtained.

DESCRIPTION OF THE DRAWINGS

The above and other features and advantages of the present invention will become more apparent by describing in detail exemplary embodiments thereof with reference to FIG. 1, which is a graph of a change in drying rate over time of aqueous compositions prepared according to Examples 2-5 and Comparative Examples 2-4.

BEST MODE

Hereinafter, an aqueous composition for preparing a hard capsule according to an embodiment of the present invention is described in detail.

An aqueous composition (hereinafter, referred to as [a first composition]) for preparing a hard capsule according to an embodiment of the present invention includes a water-soluble cellulose ether, an alcohol, and water.

The water-soluble cellulose ether is a major component of the first composition. The water-soluble cellulose ether is derived from cellulose that is a vegetable material, and is not harmful for the human body. The term "cellulose ether" used herein refers to a cellulose derivative prepared by etherifying a hydroxy group of cellulose by using an etherifying agent.

The first composition may include 10 to 25 wt % of the water-soluble cellulose ether. When the amount of the water-soluble cellulose ether is within this range, an appropriate level of viscosity may be obtained. Thus, bubbles may be easily removed from the aqueous composition, and an appropriate thickness of capsules may be obtained.

The water-soluble cellulose ether may include hydroxypropyl methylcellulose (HPMC), hydroxyethyl methylcellulose (NEMC), methylcellulose (MC), or a mixture of two or more of these.

The alcohol may help the water-soluble ether liquefy (i.e., dissolve) in the first composition. This process is described in more detail as follows: when the water-soluble cellulose ether is added to low temperature (20 to 30° C.) water, a part of the water-soluble cellulose ether that directly contacts water dissolves and a part of the water-soluble cellulose ether that does not directly contact water aggregates to form a lump, and when the water-soluble cellulose ether is added to high temperature (40 to 70° C.) water, even the part of the water-soluble cellulose ether that directly contacts water does not dissolve well. However, the alcohol is mixed with water to form an aqueous alcohol solution, and the water-soluble cellulose ether dissolves well in not only a low temperature (20 to 30° C.) aqueous alcohol solution but also a high temperature (40 to 70° C.) aqueous alcohol solution.

The first composition may include 5 to 30 wt % of the alcohol. When the amount of the alcohol is within this range, solubility of cellulose ether increases and an evaporation speed of the alcohol during the preparation of a capsule is at an appropriate level so that a wrinkle-free smooth capsule film may be obtained.

The alcohol may include ethanol, methanol, isopropanol, butanol, or a mixture of two or more of these.

The first composition may further include 0.05 to 5.0 wt % of a gelation agent. When the amount of the gelation agent is within this range, a viscosity of the first composition may appropriately increase, and thus a hard capsule formed by using the gelation agent may have increased elongation at break and decreased brittleness.

The gelation agent may include a water-soluble gum.

The water-soluble gum may include Carrageenan, Gellan gum, Xanthan gum, Pectin, or a mixture of two or more of these.

The first composition may further include more than 0 wt % and up to 1.0 wt % of a gelation aid. When the amount of the gelation aid is within this range, a gelation ability of the gelation agent may improve and thus, the first composition may have excellent capsule moldability, and a haze-free hard capsule may be obtained.

The gelation aid may include potassium chloride, potassium acetate, calcium chloride, or a mixture of two or more of these.

The first composition may further include 0.05 to 5.0 wt % of a plasticizer. When the amount of the plasticizer is within this range, a hard capsule with high elongation at break may be obtained.

The plasticizer may include glycerol, sorbitol, propylene glycol, polyethylene glycol or a mixture of two or more of these.

When the first composition is heated to a capsule molding temperature (40 to 70° C.), the water-soluble cellulose ether may be completely dissolved. Due to the complete dissolution of the water-soluble cellulose ether, the first composition may have the following advantages: a shorter preparation time; higher homogeneity, uniform viscosity and no layer-separation even during a period of long-term storage; uniform viscosity for all production lots; higher capsule moldability due to the absence of non-dissolved materials (for example, cellulose ether) that suppress performance of a gelation agent and optionally, a gelation aid; reduction of the amount of a gelation agent (and optionally, gelation aid) due to a high degree of mixing of cellulose ether and the gelation agent (and optionally, gelation aid); a high filtering efficiency in a subsequent filtering process for removing foreign materials from the first composition; a higher drying speed when a drying process for removing a solvent component from the aqueous composition doped on a substrate (e.g., mold pin) is performed in a capsule molding process; and a higher production yield of a hard capsule due to shorter preparation time and drying time for the first composition.

Another aspect of the present invention provides a hard capsule prepared by using the first composition. For example, the hard capsule may be prepared by immersing a room temperature (20 to 30° C.) mold pin in the first composition that has been heated to a high temperature (40 to 70° C.), and then taking the mold pin out of the first composition and drying the mold pin (referred to as 'cold pin process').

The hard capsule has a high quality (elasticity, glossiness, disintegrability, or the like) due to the absence of a foreign material, such as fiber, in the first composition, and the quality thereof is kept constant for all production lots.

The hard capsule may be gastric juice soluble.

Hereinafter, a method of preparing the first composition is described in detail.

The method of preparing the first composition includes preparing a cellulose ether solution that includes water, an alcohol, and water-soluble cellulose ether, and that is maintained at a first temperature (40 to 70° C.) that is higher than an atmospheric temperature (0 to 39° C.). In detail, the method includes mixing water and an alcohol to prepare an aqueous alcohol solution (S1), heating the aqueous alcohol solution (S2), dissolving water-soluble cellulose ether in the heated aqueous alcohol solution to prepare a cellulose ether solution (S3), aging the cellulose ether solution (S4), and adding a gelation agent to the resultant (S5).

In the process (S2), the heating of the aqueous alcohol solution may be performed from room temperature (20 to 30° C.) to a temperature of 40 to 70° C. The process (S2) is performed to allow the water-soluble cellulose ether to be dispersed well in the aqueous alcohol solution in the process (S3) so that the water-soluble cellulose ether is easily dissolved, without aggregating. When the heating temperature is within this range, the gelation agent (and optionally, gelation aid) may have high capsule moldability without solidification, and an increase in energy costs resulting from unnecessary heating may be minimized.

The process (S3) may be performed by slowly adding the water-soluble cellulose ether to the heated aqueous alcohol solution for a predetermined period of time (for example, 1 to 2 hours) while stirring (for example, 300 rpm).

However, the present invention is not limited thereto. For example, instead of the processes (S1 to S3), water-soluble cellulose ether may be dissolved in water (or an alcohol) to prepare a first cellulose ether solution, and then an alcohol (or water) is added to the cellulose ether solution to prepare a second cellulose ether solution. Also, in this case, (i) a water and/or an alcohol which is heated in advance is used in the procedure of the preparation of the first and second cellulose ether solutions, or (ii) the water-soluble cellulose ether is dissolved in a room temperature (about 25° C.) water (or an alcohol) to prepare a first cellulose ether solution, and then the first cellulose ether solution is heated and a room temperature alcohol (or water) is added thereto to prepare a second cellulose ether solution.

The aging process (S4) of the cellulose ether solution may be performed at a temperature of 40 to 70° C. for 2 to 12 hours. When the aging process (S4) is performed for this time range, bubbles may be sufficiently removed from the resultant and a composition of the resultant may be homogeneous.

In the process (S4), a gelation aid and/or a plasticizer, in addition to the gelation agent, may be further added to the resultant.

At least one process of the processes (S1 to S5) may be performed while stirring.

The process (S5) may be additionally followed by removing bubbles from the first composition. This process (S5) may be performed by stirring.

The functions, kinds, and amounts of the alcohol, the water-soluble cellulose ether, the gelation agent, the gelation aid, and the plasticizer are already described above, and thus explanations thereof will be omitted herein.

Hereinafter, a method of recycling a hard capsule scrap, according to an embodiment of the present invention, will be described in detail.

A method of recycling a hard capsule scrap according to an embodiment of the present invention includes preparing an aqueous composition (hereinafter, referred to as [a second composition]) for preparing a recycled hard capsule by dissolving the hard capsule scrap including a water-soluble cellulose ether in a mixed solution (also referred to as [aqueous alcohol solution]) including water and an alcohol. The term "hard capsule scrap" used herein refers to a waste material (that is, the remains after cutting) produced in the manufacturing process of a hard capsule, that is, a material that is formed of the same material as that of the hard capsule. In detail, a primarily molded hard capsule is secondarily trimmed (that is, unnecessary parts of the hard capsule are removed by cutting) to complete the preparation of a hard capsule having a target appearance, and the cut parts are referred to as a hard capsule scrap.

The kinds and functions of the water-soluble cellulose ether and the alcohol are the same as or similar to those of the water-soluble cellulose ether and the alcohol included in the first composition, and accordingly, a detailed description thereof will be omitted herein.

The hard capsule scrap may include 90 to 95 parts by weight of the water-soluble cellulose ether, 0.05 to 5.0 parts by weight of a gelation agent, 0 to 1.0 parts by weight of a gelation aid, and 1.0 to 5.0 parts by weight of the water.

The kinds and functions of the gelation agent and the gelation aid are the same as or similar to those of the gelation agent and the gelation aid included in the first composition, and accordingly, a detailed description thereof will be omitted herein.

The step of preparing the second composition may be performed by dissolving an additional water-soluble cellulose ether together with the hard capsule scrap in the aqueous alcohol solution.

According to another embodiment, the step of preparing the second composition may be performed by mixing (i) a solution prepared by dissolving the hard capsule scrap in an aqueous alcohol solution with (ii) a solution prepared by dissolving an additional water-soluble cellulose ether in an aqueous alcohol solution.

According to another embodiment, the step of preparing the second composition may be performed by preparing two or more solutions by dissolving the hard capsule scrap in an aqueous alcohol solution, and then mixing the two or more solutions at a predetermined ratio.

The additional water-soluble cellulose ether may be the same as or similar to the water-soluble cellulose ether included in the hard capsule scrap. The additional water-soluble cellulose ether may also dissolve well in a room temperature (20 to 30° C.) and high temperature (40 to 70° C.) aqueous alcohol solutions.

In detail, the step of preparing the second composition may include preparing an aqueous alcohol solution by mixing water and an alcohol (S10), heating the aqueous alcohol solution (S20), and dissolving the hard capsule scrap and optionally, the additional water-soluble cellulose ether in the heated aqueous alcohol solution to prepare a cellulose ether-containing solution (S30).

In detail, the step of preparing the second composition is similar to the step of preparing the first composition which is described above. Accordingly, hereinafter, only a difference between these two steps will be described.

First, in the step of preparing the second composition, as a raw material, the hard capsule scrap is used instead of a separate water-soluble cellulose ether, and the additional water-soluble cellulose ether is used as an aid material. This is because the hard capsule scrap already includes a water-soluble cellulose ether.

The step of preparing the second composition may further include maintaining the cellulose ether-containing solution which is prepared in the operation (S30) at a temperature of 40 to 70° C. for 2 to 12 hours (S40) (hereinafter referred to as "aging step").

The aging step (S40) may be performed without a separate gelation agent and a separate gelation aid. This is because the hard capsule scrap may already include a gelation agent and a gelation aid.

However, the step of preparing the second composition may further include, after the aging step (S40), adding at least one of an additional gelation agent and an additional gelation aid (for example, an additional gelation agent and optionally, an additional gelation aid) to the resultant of the aging step (S40). The additional gelation agent and the additional gelation aid may, respectively, be the same as or similar to the gelation agent and the gelation aid which are included in the hard capsule scrap.

At least one of the additional gelation agent and the additional gelation aid may be added to at least one step selected from all sub steps included in the step of preparing the second composition.

The hard capsule scrap may further include a plasticizer. The plasticizer may be the same as or similar to the plasticizer included in the first composition.

Also, an additional plasticizer may be further added to at least one steps selected from all sub steps included in the step of preparing the second composition. The additional plasticizer may be the same as or similar to the plasticizer included in the hard capsule scrap.

Components of the second composition, and amounts thereof, and advantages in preparing the second composition, and advantages of properties of the second composition may be the same as or similar to those of the first composition described above. Accordingly, a detailed description of these will be omitted herein.

The method of recycling a hard capsule scrap may further include coating the second composition on a substrate and drying the second composition. The coating and drying steps of the second composition on a substrate are the same as the coating and drying of the first composition on a substrate to form a hard capsule. Accordingly, a detailed description of the coating and drying steps will be omitted herein.

MODE OF THE INVENTION

Herein, the present invention is described in detail with reference to examples, but is not limited to the examples.

Examples 1-1 to 1-4 and Comparative Example 1-1: Evaluation of High Temperature Solubility of Cellulose Ether Ethanol was mixed with water (purified water) at ratios shown in Table 1 to prepare aqueous ethanol solutions. Thereafter, each of the aqueous ethanol solutions was heated to a temperature shown in Table 1, and then hydroxypropyl methylcellulose (HPMC)(available from Samsung Fine Chemical Co., Ltd., AW4) was dissolved by addition of an amount thereof as shown in Table 1 to the aqueous ethanol solution. 4 hours after HPMC was completely dissolved, appearances of the resultant were identified with the naked eye, and results thereof were evaluated based on four levels. The evaluation results are shown in Table 1.

(Evaluation of Appearances of the Resultant)

◉: HPMC is very quickly dissolved, and appearances of the resultant are clear and transparent.

○: HPMC is relatively quickly dissolved, and appearances of the resultant are clear and transparent.

Δ: HPMC is relatively slowly dissolved, and appearances of the resultant are slightly hazy.

x: HPMC is not dissolved, and appearances of the resultant are strongly hazy.

TABLE 1

|  | Amounts (wt %) | | | Temperature of aqueous ethanol solution (□) | appearances |
|---|---|---|---|---|---|
|  | Water | Ethanol | HPMC | | |
| Example 1-1 | 60 | 20 | 20 | 60 | ◉ |
| Example 1-2 | 65 | 15 | 20 | 60 | ◉ |
| Example 1-3 | 70 | 10 | 20 | 60 | ○ |
| Example 1-4 | 75 | 5 | 20 | 60 | Δ |
| Comparative Example 1-1 | 80 | 0 | 20 | 60 | X |

Referring to Table 1, in the case of the resultants prepared according to Examples 1-1 to 1-4, HPMC was dissolved well and appearances and viscosities of the resultants were at appropriate levels. In the case of the resultants prepared according to Comparative Example 1-1, HPMC exists in a non-soluble state and appearances of the resultants were at inappropriate levels.

Examples 2-1 to 2-5: Evaluation on Gelation Degree and Drying Speed of Aqueous Composition K-carrageenan (Korea Carragheen, HG404), which is a gelation agent, and potassium chloride, which is a gelation aid, were added according to ratios shown in Table 2 below to the resultant prepared according to Example 1-2 to obtain aqueous compositions. Thereafter, gelation degrees of the respective aqueous compositions were measured according to a method described below, and results thereof are shown in Table 2. Also, the drying speed of the aqueous composition prepared according to Example 2-5 was measured according to a method described below, and results thereof are shown in Table 3 below.

(Gelation Degree Evaluation)

The respective aqueous compositions were sampled by using 2 ml-capacity syringes, and then, the obtained samples were sprayed at once onto a glass plate that was perpendicularly erected. After the spraying, when the flow of the respective aqueous compositions flowing along the glass plate stopped, flow lengths of the respective aqueous compositions on the glass plate were measured. Herein, the shorter flow length, the higher the gelation degree.

(Drying Speed Evaluation)

A mold pin was immersed in the aqueous composition prepared according to Example 2-5. Thereafter, the mold pin was taken out from the aqueous composition and left to sit at a temperature of 25° C. and in 55% RH (relative humidity) while a weight change of the mold pin was measured over time. Then, from the weight change of the mold pin, a drying rate of the aqueous composition was calculated. Herein, the higher drying rate change over time, the higher drying speed. The change in weight of the mold pin over time and the change in the drying rate of the aqueous solution over time are shown in Table 3 below. Also, the change in the drying rate of the aqueous composition over time is shown in FIG. 1.

Comparative Examples 2-1 to 2-3: Evaluation of Gelation Degree and Drying Speed of Aqueous Compositions Aqueous compositions of Comparative Examples 2-1 to 2-3 were prepared in the same manner as in Examples 2-1 to 2-5, except that the resultant prepared according to Comparative Example 1-1 was used instead of the resultant prepared according to Example 1-2, and amounts of K-Carrageenan and optionally, potassium chloride were changed. A degree of gelation of each of the aqueous compositions was evaluated, and results thereof are shown in Table 2. Also, a drying rate of the aqueous compositions over time were evaluated in the same manner as in Example 2-5, except that the aqueous composition prepared according to Comparative Example 2-4 was used instead of the aqueous composition prepared according to Example 2-5, and results thereof are shown in Table 3 below. Also, a change in a drying rate of the aqueous compositions over time is shown in FIG. 1.

TABLE 2

|  | Amounts (wt %) | | Gelation degree (cm) |
|---|---|---|---|
|  | K-Carrageenan | potassium chloride | |
| Example 2-1 | 2.0 | 0.0 | 7.0 |
| Example 2-2 | 1.5 | 0.0 | 7.5 |
| Example 2-3 | 1.0 | 0.0 | 9.0 |
| Example 2-4 | 0.8 | 0.0 | 10.0 |
| Example 2-5 | 1.0 | 0.1 | 7.5 |
| Comparative Example 2-1 | 2.0 | 0.0 | 10.0 |
| Comparative Example 2-2 | 1.5 | 0.0 | 11.1 |
| Comparative Example 2-3 | 1.0 | 0.1 | 11.5 |
| Comparative Example 2-4 | 1.0 | 0.5 | 7.5 |

Referring to Table 2, it was confirmed that the aqueous compositions prepared according to Examples 2-1 to 2-5 had higher gelation degrees than the aqueous compositions prepared according to Comparative Examples 2-1 to 2-3 when the same or similar amounts of a gelation agent (K-Carrageenan) and a gelation aid (potassium chloride) were used. Accordingly, when an aqueous composition was manufactured according to an embodiment of the present invention, compared to when an aqueous composition is prepared according to a conventional method, lesser amounts of the gelation agent and the gelation aid may be used. Also, it was confirmed that there were such amounts of the gelation agent and the gelation aid and mixed ratios thereof which are appropriate for increasing a gelation degree of the aqueous composition. Also, in the case of the aqueous composition prepared according to Comparative Example 2-4, a gelation degree of the aqueous composition was high, but HPMC was not dissolved, as shown in Table 1. Accordingly, capsule moldability of the aqueous composition may decrease, and a formed hard capsule may have poor quality.

TABLE 3

| Time (min) | Weight of mold pin (g) Example 2-5 | Weight of mold pin (g) Comparative Example 2-4 | Total weight of mold pin and aqueous composition (g) Example 2-5 | Total weight of mold pin and aqueous composition (g) Comparative Example 2-4 | Weight of aqueous composition (g) Example 2-5 | Weight of aqueous composition (g) Comparative Example 2-4 | Drying rate (wt %) Example 2-5 | Drying rate (wt %) Comparative Example 2-4 |
|---|---|---|---|---|---|---|---|---|
| 0 | 12.54 | 12.54 | 13.30 | 13.19 | 0.76 | 0.65 | 0.0 | 0.0 |
| 20 | 12.54 | 12.54 | 13.25 | 13.18 | 0.71 | 0.64 | 6.58 | 1.54 |
| 40 | 12.54 | 12.54 | 13.19 | 13.14 | 0.65 | 0.60 | 14.47 | 7.69 |
| 60 | 12.54 | 12.54 | 13.09 | 13.09 | 0.55 | 0.55 | 27.63 | 15.38 |
| 120 | 12.54 | 12.54 | 12.98 | 13.04 | 0.44 | 0.50 | 42.11 | 23.08 |

Referring to Table 3 and FIG. 1, it was confirmed that the aqueous composition prepared according to Example 2-5 had a higher drying speed than the aqueous composition prepared according to Comparative Example 2-4.

Example 3-1 and Comparative Example 3-1:
Evaluation on Solubility and Haze of Hard Capsule A mold pin was immersed in each of the aqueous compositions (temperature: 60° C.) prepared according to Example 2-5 and Comparative Example 2-4. Thereafter, the mold pins were taken out from the aqueous compositions and then left to sit at a temperature of 25° C. and in 55% RH (relative humidity) for 1 hour to remove a solvent component from the aqueous composition by drying, thus obtaining hard capsules. Thereafter, the solubility and haze of each of the hard capsules were evaluated according to methods described below, and results thereof are shown in Tables 4 and 5 below.

(Evaluation of Dissolution Speed of Hard Capsule) 50 ml of water (purified water) was added into a 100 ml Erlenmeyer flask, and then a temperature of the water was maintained at 37° C. Each of the respective hard capsules was then added into the Erlenmeyer flask, and then while the Erlenmeyer flask was intermittently shaken, the dissolution states of the respective hard capsules were observed. For each of the hard capsules, a period of time (i.e., a dissolution time) from a time when a hard capsule was added into the Erlenmeyer flask to a time when the hard capsule was completely dissolved was recorded, and results thereof are shown in Table 4 below. Herein, the shorter dissolution time, the higher the dissolution speed.

TABLE 4

| | Example 3-1 | Comparative Example 3-1 |
|---|---|---|
| Dissolution time | 6 minutes and 15 seconds | 8 minutes and 26 seconds |

Referring to Table 4, the hard capsule prepared according to Example 3-1 had a higher dissolution speed than the hard capsule prepared according to Comparative Example 3-1.

(Evaluation on Haze of Hard Capsule)

Each of the hard capsules was added into a 40 ml vial, and then the vials were placed in a thermo-hygrostat having conditions of a temperature 40° C. and 75% RH (relative humidity). Thereafter, each of the hard capsules was observed with the naked eye, and a degree of occurrence of haze was evaluated based on three levels as below; results thereof are shown in Table 5.
⊚: No change (i.e., transparency).
○: Changed into being partially hazy.
Δ: Changed into being generally hazy.

TABLE 5

| Elapsed time | Example 3-1 | Comparative Example 3-1 |
|---|---|---|
| At the beginning | ⊚ | ⊚ |
| First week | ⊚ | ⊚ |
| Second week | ⊚ | ⊚ |
| Third week | ⊚ | ○ |
| Fourth week | ⊚ | Δ |

Referring to Table 5, the hard capsule prepared according to Example 3-1 did not exhibit haze even after the hard capsule had been stored for a long period of time, but the hard capsule prepared according to Comparative Example 3-1 exhibited haze (after three weeks had elapsed.

Examples 4-1 and 4-2 and Reference Example 1-1:
Preparation of Aqueous Composition for Preparing Hard Capsule Aqueous ethanol solutions were prepared by mixing ethanol and water (purified water) at ratios shown in Table 6 below. Thereafter, the aqueous ethanol solutions were heated to temperatures shown in Table 6 below, and then, a hard capsule scrap and/or hydroxypropylmethylcellulose (HPMC) (AW4 available from Samsung Fine Chemical Co., Ltd.) were added at ratios shown in Table 6 below to the aqueous ethanol solutions and then dissolved therein. In Examples 4-1 and 4-2 and Reference Example 1-1, to obtain an aqueous composition for preparing a hard capsule containing 1.5 wt % of K-carrageenan, an appropriate amount of K-carrageenan (Korea Carragheen, HG404) was further added to the aqueous ethanol solution. As a result, the aqueous compositions for preparing a hard capsule prepared according to Examples 4-1 and 4-2 and Reference Example 1-1 contained about 20 wt % HPMC or 1.5 wt % K-carrageenan.

TABLE 6

| | Content ratio (wt %) Water | Content ratio (wt %) ethanol | Content ratio (wt %) hard capsule scrap[*1] | Content ratio (wt %) HPMC | Temperature of aqueous ethanol solution (° C.) |
|---|---|---|---|---|---|
| Example 4-1 | 70 | 10 | 20 | 0 | 60 |
| Example 4-2 | 70 | 10 | 10 | 10 | 60 |
| Reference Example 1-1 | 70 | 10 | 0 | 20 | 60 |

[*1]Hard capsule scrap that contained 92 wt % HPMC (AW4, available from Samsung Fine Chemical Co., Ltd.), 1.2 wt % of K-carrageenan (Korea Carragheen, HG404), 0.08 wt % of KCl, 1.72 wt % of glycerol, and 5 wt % of water.

Evaluation Example

Regarding Examples 4-1 and 4-2 and Reference Example 1-1, 4 hours after the hard capsule scrap and/or HPMC was completely dissolved, the appearance of the resultant (that is, an aqueous composition for preparing a hard capsule) was observed with naked eyes and evaluated in the same manner as described in Examples 1-1 to 1-4 and Comparative Example 1-1, and results thereof are shown in Table 7 below. Also, strength of gels formed from the each aqueous compositions for preparing a hard capsule prepared according to Examples 4-1 and 4-2 and Reference Example 1-1 and properties of films prepared from the aqueous compositions were measured according to the following method, and results thereof are shown in Table 7 below.

(Evaluation of Gel Strength)

The aqueous compositions for preparing a hard capsule which had been maintained at a temperature of 60° C. were gelated by cooling the aqueous compositions to room temperature (about 25° C.). Thereafter, strength of the gels formed from the aqueous compositions for preparing a hard capsule was measured by using a Texture Analyser (Brookfield, CT3-4500, Probe No: TA10), and results thereof are shown in Table 7 below.

(Evaluation of Properties of Film)

The aqueous compositions for preparing a hard capsule which had been maintained at a temperature of 60° C. were coated on a glass substrate by using a film caster (directly manufactured by Samsung Fine Chemical Co., Ltd.). Then, the glass substrate with the aqueous compositions for preparing a hard capsule coated thereon were dried at room temperature (25° C.) for 24 hours to obtain a film having a thickness of 100 μm. Thereafter, the respective films were cut to a size of 1 cm*10 cm, and then tensile strengths of the films were measured by using a LLOYD Instrument testing machine (LRX plus, LLOYD Instrument, UK). Also, the respective films were cut to a size of 4 cm*5 cm, and then, hardness thereof was measured by using a Texture Analyzer (Brookfield, CT3-4500, Probe No. TA-39), and results thereof are shown in Table 7 below.

TABLE 7

|  | Example 4-1 | Example 4-2 | Reference Example 1-1 |
|---|---|---|---|
| Appearance | ○ | ◎ | ◎ |
| Gel strength (g) | 110 | 120 | 130 |
| Tensile strength (N/mm$^2$) | 65 | 62 | 66 |
| Film hardness (g) | 3,230 | 3,110 | 3,200 |

Referring to Table 7, the aqueous compositions for preparing a hard capsule prepared by using a hard capsule scrap and optionally, HPMC according to Examples 4-1 and 4-2, like the aqueous composition for preparing a hard capsule prepared by using only HPMC according to Reference Example 1-1, the hard capsule scrap and the HPMC, which was optionally used, were dissolved well, and thus, the appearance of the aqueous compositions looked well. Also, compared to the gel formed from the aqueous composition for preparing a hard capsule prepared according to Reference Example 1-1, at the same amount of the gelation agent (K-carrageenan), the gels formed from the aqueous compositions for preparing a hard capsule prepared according to Examples 4-1 and 4-2 may have a gel strength (≥100 g) that was appropriate for the preparation of a hard capsule, although the gel strength was slightly low. Also, the films prepared from the aqueous compositions for preparing a hard capsule prepared by using a hard capsule scrap and optionally HPMC according to Examples 4-1 and 4-2, like the film prepared from the aqueous composition for preparing a hard capsule prepared by using only HPMC according to Reference Example 1-1, had appropriate levels of tensile strength and film hardness.

An aqueous composition for preparing a hard capsule according to an embodiment of the present invention includes water-soluble cellulose ether and an alcohol. Due to the inclusion of water-soluble cellulose ether and water, cellulose ether may directly dissolve in water at not only relatively low temperature (for example, 0 to 40° C.) but also relatively high temperature (for example, 40 to 70° C.). Accordingly, the preparation time for the aqueous composition may reduce, a drying time for drying the aqueous composition when molding a capsule may reduce, and a production yield of a hard capsule, which is a final product, may increase. Also, a degree of mixing of cellulose ether and a gelation agent (and optionally, a gelation aid) may improve, and thus, even when the gelation agent (and optionally, a gelation aid) is used in small amounts, a high-quality hard capsule may be obtained.

According to a method of recycling a hard capsule scrap, the manufacturing costs for a hard capsule and the disposal costs for a hard capsule scrap may reduce, and the environmental pollution may reduce, and a high-quality hard capsule may be obtained.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. An aqueous composition for preparing a hard capsule, the aqueous composition comprising a cellulose ether solution, the cellulose ether solution comprising:
a water-soluble cellulose ether;
an alcohol; and
water,
wherein non-dissolved materials are absent from the aqueous composition,
wherein the aqueous composition comprises 10 to 25 wt % of the water-soluble cellulose ether, 5 to 30 wt % of the alcohol and 0.05 to 5.0 wt % of a gelation agent; wherein the alcohol comprises ethanol, methanol, isopropanol, butanol, or a mixture of two or more of these; wherein the water-soluble cellulose ether comprises hydroxypropyl methylcellulose(HPMC), hydroxyethyl methylcellulose(HEMC), methylcellulose(MC), or a mixture of two or more of these.

2. The aqueous composition of claim 1, wherein the gelation agent is selected from Carrageenan, Gellan gum, Xanthan gum, Pectin, and a mixture of two or more of these.

3. The aqueous composition of claim 1, wherein the aqueous composition further comprises more than 0 wt % and up to 1.0 wt % of a gelation aid selected from potassium chloride, potassium acetate, calcium chloride, and a mixture of two or more of these.

4. A method of preparing an aqueous composition for preparing a hard capsule, the method comprising preparing a cellulose ether solution that contains water, an alcohol and a water-soluble cellulose ether, and that is maintained in a range of 40 to 70° C. higher than an atmospheric temperature, and adding a gelation agent to the cellulose ether solution; wherein the alcohol comprises ethanol, methanol, isopropanol, butanol, or a mixture of two or more of these, wherein non-dissolved materials are absent from the aqueous composition,
wherein the aqueous composition comprises 10 to 25 wt % of the water-soluble cellulose ether, 0.05 to 5.0 wt % of a gelation agent, and 5 to 30 wt % of the alcohol; wherein the water-soluble cellulose ether comprises hydroxypropyl methylcellulose(HPMC), hydroxyethyl methylcellulose(HEMC), methylcellulose(MC), or a mixture of two or more of these.

5. A hard capsule prepared by using the aqueous composition of claim 1.

6. A method of recycling a hard capsule scrap, the method comprising preparing an aqueous composition for preparing a recycled hard capsule by dissolving the hard capsule scrap containing water-soluble cellulose ether in a mixed solution including water and an alcohol,
wherein non-dissolved materials are absent from the aqueous composition,
wherein the aqueous composition comprises 10 to 25 wt % of the water-soluble cellulose ether, 5 to 30 wt % of the alcohol and 0.05 to 5.0 wt % of a gelation agent; wherein the alcohol comprises ethanol, methanol, isopropanol, butanol, or a mixture of two or more of these, wherein the temperature of the aqueous composition is in a range of 40 to 70° C.; wherein the water-soluble cellulose ether comprises hydroxypropyl methylcellulose(HPMC), hydroxyethyl methylcellulose(HEMC), methylcellulose(MC), or a mixture of two or more of these.

7. The method of claim 6, wherein
the hard capsule scrap includes 90 to 95 parts by weight of the water-soluble cellulose ether, 0.05 to 5.0 parts by weight of a gelation agent, 0 to 1.0 parts by weight of a gelation aid, and 1.0 to 7.0 parts by weight of water.

8. The method of claim 6, wherein
the step of preparing the aqueous composition for preparing a recycled hard capsule comprises dissolving additional water-soluble cellulose ether together with the hard capsule scrap in a mixed solution including water and an alcohol.

9. The method of claim 6 or 8, further comprising
maintaining the aqueous composition for preparing a recycled hard capsule at a temperature of 40 to 70° C. for 2 to 12 hours.

10. The method of claim 9, further comprising
adding at least one of an additional gelation agent and an additional gelation aid to the aqueous composition for preparing a recycled hard capsule.

11. The method of claim 9, further comprising
coating the aqueous composition for preparing a recycled hard capsule on a substrate and drying the aqueous composition.

12. The method of claim 6, wherein the aqueous composition for preparing a recycled hard capsule further comprises
more than 0 wt % and up to 1.0 wt % of the gelation aid.

* * * * *